US00PP27290P2

(12) United States Plant Patent
Hooijman

(10) Patent No.: US PP27,290 P2
(45) Date of Patent: Oct. 25, 2016

(54) ROSE PLANT NAMED 'ESM R107'

(50) Latin Name: *Rosa hybrida*
Varietal Denomination: ESM R107

(71) Applicant: Aloysius A. J. Hooijman, Aalsmeer (NL)

(72) Inventor: Aloysius A. J. Hooijman, Aalsmeer (NL)

(73) Assignee: Esmeralda Breeding B.V., Aalsmeer (NL)

( * ) Notice: Subject to any disclaimer, the term of this patent is extended or adjusted under 35 U.S.C. 154(b) by 178 days.

(21) Appl. No.: 14/121,557

(22) Filed: Sep. 17, 2014

(51) Int. Cl.
*A01H 5/02* (2006.01)

(52) U.S. Cl.
USPC ..... Plt./136

(58) Field of Classification Search
USPC ..... Plt./136
See application file for complete search history.

*Primary Examiner* — Keith Robinson
(74) *Attorney, Agent, or Firm* — C. A. Whealy

(57) ABSTRACT

A new and distinct cultivar of Rose plant named 'ESM R107', characterized by its upright, long and strong flowering stems; vigorous growth habit and high productivity; dark green-colored leaves; peach pink-colored flowers that are held on strong pedicels on relatively large sprays; freely flowering habit; and excellent postproduction longevity.

1 Drawing Sheet

Botanical designation: *Rosa hybrida.*
Cultivar denomination: 'ESM R107'.

BACKGROUND OF THE INVENTION

The present Invention relates to a new and distinct cultivar of Rose plant, botanically known as *Rosa hybrida*, commercially used as a cut flower Rose plant, and hereinafter referred to by the name 'ESM R107'.

The new Rose plant is a product of a planned breeding program conducted by the Inventor in El Quinche, Pichincha, Ecuador. The objective of the breeding program was to develop new cut flower Rose varieties with attractive flowers and excellent postproduction longevity.

The new Rose plant originated from a cross-pollination made by the Inventor in November, 2008 of a proprietary Rose selection identified as Line 188, not patented, as the female, or seed, parent with a proprietary Rose selection identified as Line 222, not patented, as the male, or pollen, parent. The new Rose plant was discovered and selected by the Inventor as a single flowering plant within the progeny of the stated cross-pollination in a controlled greenhouse environment in El Quinche, Pichincha, Ecuador in September, 2009.

Asexual reproduction of the new Rose plant by bud grafting in El Quinche, Pichincha, Ecuador since March, 2010 has shown that the unique features of this new Rose plant are stable and reproduced true to type in successive generations of asexual reproduction.

SUMMARY OF THE INVENTION

Plants of the new Rose have not been observed under all possible combinations of environmental conditions and cultural practices. The phenotype may vary somewhat with variations in environmental conditions such as temperature and light intensity, without however, any variance in genotype.

The following traits have been repeatedly observed and are determined to be the unique characteristics of 'ESM R107'. These characteristics in combination distinguish 'ESM R107' as a new and distinct Rose plant:

1. Upright, long and strong flowering stems.
2. Vigorous growth habit and high productivity.
3. Dark green-colored leaves.
4. Peach pink-colored flowers that are held on strong pedicels on relatively large sprays.
5. Freely flowering habit with typically about seven to nine flowers per spray.
6. Excellent postproduction longevity.

Plants of the new Rose differ from plants of the female parent selection in the following characteristics:

1. Plants of the new Rose have longer flowering stems than plants of female parent selection.
2. Stems of plants of the new Rose have fewer thorns than stems of plants of the female parent selection.
3. Flowers of plants of the new Rose have more petals than flowers of plants of the female parent selection.
4. Plants of the new Rose and the female parent selection differ in flower color as plants of the female parent selection have orange-colored flowers.

Plants of the new Rose differ from plants of the male parent selection in the following characteristics:

1. Plants of the new Rose are slightly smaller than plants of the male parent selection.
2. Plants of the new Rose and the male parent selection differ in flower color as plants of the male parent selection have orange-colored flowers.

Plants of the new Rose can be compared to plants of *Rosa hybrida* 'Esm Durazno', disclosed in U.S. Plant Pat. No. 21,004. In side-by-side comparisons conducted in El Quinche, Pichincha, Ecuador, plants of the new Rose differed from plants of 'Esm Durazno' in the following characteristics:

1. Plants of the new Rose were larger than plants of 'Esm Durazno'.

2. Plants of the new Rose were more vigorous than plants of 'Esm Durazno'.
3. Plants of the new Rose were more freely branching than plants of 'Esm Durazno'.
4. Plants of the new Rose had larger leaves and leaflets than plants of 'Esm Durazno'.
5. Plants of the new Rose had larger sprays with more flowers per spray than plants of 'Esm Durazno'.
6. Plants of the new Rose and 'Esm Durazno' differed in flower color as plants of 'Esm Durazno' had light salmon pink-colored flowers.
7. Plants of the new Rose had longer pedicels than plants of 'Esm Durazno'.

BRIEF DESCRIPTION OF THE PHOTOGRAPHS

The accompanying colored photographs illustrate the overall appearance of the new Rose plant showing the colors as true as it is reasonably possible to obtain in colored reproductions of this type. Colors in the photographs may differ slightly from the color values cited in the detailed botanical description which accurately describe the colors of the new Rose plant.

The photograph on the left side of the sheet comprise side perspective and close-up views of typical flowering stems of 'ESM R107'.

The photograph at the upper right of the sheet is a close-up view of a typical developed flower of 'ESM R107'.

The photographs at the lower right of the sheet are close-up views of the upper and lower surfaces of typical leaves of 'ESM R107'.

DETAILED BOTANICAL DESCRIPTION

The aforementioned photographs, following observations and measurements describe plants grown in 10-liter containers in a polyethylene-covered greenhouse in El Quinche, Pichincha, Ecuador and under typical hydroponic Rose production practices. Plants were pinched 13 to 14 weeks after planting and were two years and 23 weeks old when the description and photographs were taken. During the production of the plants, day temperatures ranged from 16° C. to 30° C., night temperatures ranged from 12° C. to 16° C. and light levels ranged from 800 to 1,200 foot-candles. In the following description, color references are made to The Royal Horticultural Society Colour Chart, 2001 Edition, except where general terms of ordinary dictionary significance are used.

Botanical classification: *Rosa hybrida* 'ESM R107'.

Parentage:

*Female, or seed, parent*.—Proprietary seedling selection of *Rosa hybrida* identified Line 188, not patented.

*Male, or pollen, parent*.—Proprietary seedling selection of *Rosa hybrida* identified Line 222, not patented.

Propagation:

*Type*.—By bud grafting.

*Time to initiate roots, summer*.—About 15 days at temperatures about 26° C. to 30° C.

*Time to produce a rooted young plant, summer*.—About 30 days at temperatures about 22° C. to 26° C.

*Root description*.—Fibrous, medium in thickness; close to N199B in color.

*Rooting habit*.—Moderately freely branching; medium density.

Plant description:

*Plant and growth habit*.—Perennial shrub; upright and strong flowering stems; typically grown as a spray-type cut flower; vigorous growth habit.

*Branching habit*.—Freely basal branching habit; highly productive with about twelve flowering stems developing per plant per year.

*Plant height*.—About 131 cm.

*Plant width (spread)*.—About 64 cm.

*Lateral branches*.—Quantity: Freely branching habit with about 21 lateral branches developing per plant. Length: About 93 cm. Diameter: About 7.2 mm. Internode length: About 5.1 cm. Texture: Smooth, glabrous; older stems, woody. Color: Close to 146A and N199B. Thorns: Density: Low. Shape: Triangular with sharp acuminate apices; slightly incurved and flat. Height: About 8 mm. Length, at base: About 9 mm. Color, immature: Close to 175B and N199D. Color, mature: Close to 165C.

Leaf description:

*Arrangement*.—Alternate; compound with typically five to seven leaflets per leaf.

*Leaf length*.—About 19.5 cm.

*Leaf width*.—About 13.9 cm.

*Terminal leaflet length*.—About 7 cm.

*Terminal leaflet width*.—About 4.9 cm.

*Lateral leaflet length*.—About 6.7 cm.

*Lateral leaflet width*.—About 4.5 cm.

*Leaflet shape*.—Ovate.

*Leaflet apex*.—Acute.

*Leaflet base*.—Short attenuate.

*Leaflet margin*.—Serrate.

*Leaflet texture, upper and lower surfaces*.—Smooth; papery to coriaceous.

*Leaflet venation pattern*.—Pinnate.

*Leaflet color*.—Developing leaflets, upper surface: Close to between 139A and 147A. Developing leaflets, lower surface: Close to 147B. Fully expanded leaflets, upper surface: Close to 139A; venation, close to 148A. Fully expanded leaflets, lower surface: Close to 147B; venation, close to 146C.

*Petioles, leaves*.—Length: About 1.8 cm. Diameter: About 1.9 mm. Texture, upper surface: Prickly. Texture, lower surface: Smooth, glabrous. Color, upper surface: Close to 144A and 187A. Color, lower surface: Close to 146A to 146D.

*Petioles, leaflets*.—Length: About 3 cm. Diameter: About 1.2 mm. Texture, upper surface: Prickly. Texture, lower surface: Smooth, glabrous. Color, upper surface: Close to between 146A and 144A. Color, lower surface: Close to 146B to 146C.

*Stipules*.—Arrangement and appearance: Two, adnate to the petiole, leafy in appearance. Length: About 2.4 cm. Width: About 1.9 mm. Shape: Roughly deltoid. Apex: Acuminate, tapered. Base: Tapered. Margin: Serrate. Texture, upper and lower surfaces: Smooth; membranous. Venation pattern: Pinnate. Color, upper surface: Close to between 139A to 137A. Color, lower surface: Close to between 146A and 137A.

Flower description:

*Flower type and arrangement*.—Symmetrical rosette flowers; flowers typically grown as spray-types; flowers face upright; freely flowering with typically seven to nine flowers per spray.

*Flowering season*.—Plants of the new Rose flower year-round under greenhouse conditions; early flowering habit, plants begin flowering about 85 days after pinching.

*Spray diameter*.—About 17.9 cm.

*Spray height*.—About 26.6 cm.

*Flower diameter*.—About 5.9 cm.

*Flower depth* (*height*).—About 2.9 cm.

*Flower longevity*.—Excellent postproduction longevity; flowers maintain good substance for about 28 to 30 days on the plant and for about ten to twelve days as cut flowers; flowers persistent.

*Fragrance*.—None detected.

*Flower buds*.—Length: About 2.9 cm. Diameter: About 2.4 cm. Shape: Ovoid. Rate of opening: About eleven days. Color: Close to between 144A and 143A.

*Petals*.—Quantity: About 29 per flower; petals imbricate. Length: About 2.9 cm. Width: About 3.3 cm. Shape: Nearly round. Apex: Blunt. Base: Obtuse. Margin: Entire. Texture, upper and lower surfaces: Smooth, glabrous; papery to coriaceous. Color: When opening, upper surface: Close to between 179D and N170D; towards the base, close to 8B. When opening, lower surface: Close to between 179D and N170D; towards the base, close to 160A. Fully opened, upper surface: Close to 179D; towards the base, close to 3C. Fully opened, lower surface: Close to 37D; towards the base, close to 4C.

*Petaloids*.—Quantity: About seven; whorled. Length: Variable. Width: Variable. Shape: Irregularly shaped. Apex: Short acute. Base: Obtuse. Margin: Mostly uneven. Texture, upper and lower surfaces: Smooth, glabrous; papery to coriaceous. Color: When opening, upper and lower surfaces: Close to 31D and 153D. Fully opened, upper and lower surfaces: Close to 50D and 157A.

*Sepals*.—Quantity per flower: Typically five in a single whorl. Length: About 3.1 cm. Width: About 1 cm. Shape: Roughly deltoid. Apex: Tapered. Base: Truncate. Margin: Entire; ciliated and/or glandular. Texture, upper and lower surfaces: Leathery; rugose. Color: When opening, upper surface: Close to 146D. When opening, lower surface: Towards the apex, close to 144A; mid-section, close to N167B; towards the base, close to 144B. Fully opened, upper surface: Close to 146C to 146D. Fully opened, lower surface: Towards the apex, close to 144A; mid-section, close to 178B; towards the base, close to 146C.

*Pedicels*.—Length: About 4.2 cm. Diameter: About 3.2 mm. Strength: Strong. Angle: About 36° from vertical. Texture: Spiny and glandular. Color: Close to N199A.

*Reproductive organs*.—Stamens: Quantity: About 120 per flower. Anther length: About 2 mm. Anther shape: Reniform. Anther color: Close to between 153D and 160A. Filament color: Close to 153D. Pollen amount: Moderate. Pollen color: Close to 163B. Pistils: Quantity: About 115 per flower. Pistil length: About 1.3 cm. Stigma shape: Broadly reniform. Stigma color: Close to 153D. Style length: About 9 mm. Style color: Close to 145C. Receptacle height: About 9 mm. Receptacle diameter: About 8 mm. Receptacle shape: Cup-shaped. Receptacle texture: Smooth, glabrous. Receptacle color: Close to 144A. Fruits and seeds: Fruit and seed development have not been observed on plants of the new Rose.

Pathogen & pest tolerance: Plants of the new Rose have been observed to be moderately tolerant to Powdery Mildew, *Botrytis* and *Peronospora*. Plants of the new Rose have not been observed to be tolerant to pests and other pathogens common to Rose plants.

Temperature tolerance: Plants of the new Rose have been observed to tolerate temperatures ranging from 0° C. to 35° C.

It is claimed:

1. A new and distinct Rose plant named 'ESM R107' as illustrated and described.

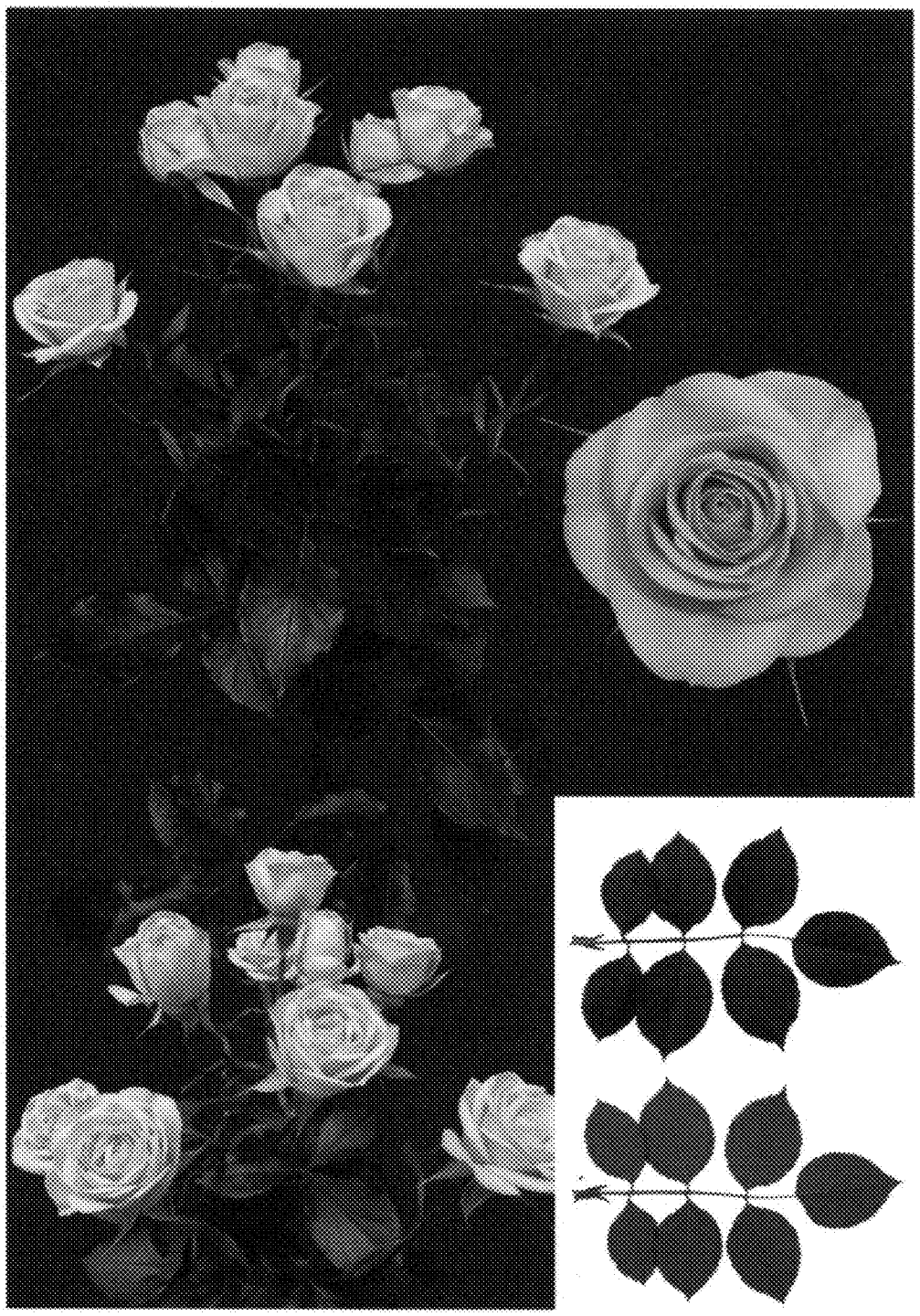

* * * * *